(12) United States Patent
deSouza et al.

(10) Patent No.: US 11,137,348 B2
(45) Date of Patent: Oct. 5, 2021

(54) METHOD AND APPARATUS FOR SULFUR FIRE-WATCH AND DETECTION

(71) Applicant: Enersul Inc., Calgary (CA)

(72) Inventors: Carlito Rolland deSouza, Calgary (CA); Trevor Michael Greer, Heritage Pointe (CA); David Alexander Shaw, Calgary (CA)

(73) Assignee: Enersul Inc., Calgary (CA)

( * ) Notice: Subject to any disclaimer, the term of this patent is extended or adjusted under 35 U.S.C. 154(b) by 83 days.

(21) Appl. No.: 16/680,805

(22) Filed: Nov. 12, 2019

(65) Prior Publication Data

US 2020/0150031 A1 May 14, 2020

Related U.S. Application Data

(60) Provisional application No. 62/760,505, filed on Nov. 13, 2018.

(51) Int. Cl.
*G01N 21/3504* (2014.01)
*G01N 33/00* (2006.01)
*G08B 17/117* (2006.01)
*G01N 22/00* (2006.01)

(52) U.S. Cl.
CPC ......... *G01N 21/3504* (2013.01); *G01N 22/00* (2013.01); *G01N 33/0063* (2013.01); *G08B 17/117* (2013.01); *G01N 2021/3531* (2013.01)

(58) Field of Classification Search
CPC .... G01N 21/3504; G01N 21/39; G01N 22/00; G01N 33/0063; G01N 2021/3531; G08B 17/117
See application file for complete search history.

(56) References Cited

U.S. PATENT DOCUMENTS

| 6,061,141 A * | 5/2000 | Goldenberg ....... G01N 21/3504 356/437 |
| 2011/0153223 A1* | 6/2011 | Gentala .................. G01N 21/31 702/24 |
| 2012/0068863 A1* | 3/2012 | Tillotson ............... G01S 13/003 340/963 |
| 2016/0349228 A1* | 12/2016 | Kester ...................... G01J 3/36 |

OTHER PUBLICATIONS

National Security Technologies, LLC, "Passive Infrared Systems for Remote Chemical Detection Assessment Report," U.S. Department of Homeland Security, Sep. 2016, pp. 1-57.
(Continued)

*Primary Examiner* — Orlando Bousono
(74) *Attorney, Agent, or Firm* — Arnold & Porter Kaye Scholer

(57) ABSTRACT

A method and system for detecting sulfur fires that comprises a remote infrared or microwave sensor to detect sulfur dioxide gas and provide an unsupervised remote daytime and nighttime sulfur fire-watch, hot spot detection, early sulfur fire prevention, sulfur fire detection, or sulfur fire control of unattended combustible sulfur blocks, sulfur stockpiles, sulfur plants, or equipment using remote sensing devices that includes detection, measurement and analysis of electromagnetic radiation to determine the presence of sulfur dioxide gas.

17 Claims, 4 Drawing Sheets

(56) References Cited

OTHER PUBLICATIONS

E. R. Bartle, "Infrared Sensor for the Remote Monitoring of SO2," U.S. Environmental Protection Agency, May 1975, Publication No. EPA-650/2-75-041, Washington, DC.
George M. Russwurm, "Long-Path Open-Path FT Infrared Monitoring of Atmospheric Gases," Compendium of Methods for the Determination of Toxic Organic Compounds in Ambient Air, Second Edition, (EPA/625/R-96/010b), Center for Environmental Research Information, Cincinnati, OH, Jan. 1999.
Jeffrey Myers et al., Environmental Technology Verification Report, "Opsis Inc. AR-500 Ultraviolet Open-Path Monitor," Battelle, Columbus, OH.
Jeffrey Myers et al., Environmental Technology Verification Report, "AIL Systems Inc. RAM 2000 Fourier Transform Infrared Open-Path Monitor," Battelle, Columbus, OH.
Texas Commission on Environmental Quality, "Literature Assessment of Remote Sensing Technologies for Detecting and Estimating Emissions for Flares and Fugitives," May 2008, ENVIRON International Corporation, Houston, Texas.
T.A. Blake et al., Chemical Emission Scenarios and Detection Limits for Active Infrared Remote Sensing, Nov. 2000, Pacific Northwest National Laboratory, Richland, WA.
Flir, "ThermoVision EFD," visited Nov. 7, 2019 at https://www.flir.com/products/thermovision-EFD, Oct. 4, 2018.
Flir, "Early Fire Detection," visited Nov. 7, 2019 at www.flir.com/automation, Jun. 2017.
Flir, "Flir Cameras Help Protect Biofuel Supply for Stockholm Area," visited Nov. 7, 2019, at www.flir.com/automation, Apr. 2016.
Judi Beck, "Capabilities of Airborne Infrared Remote Sensing Systems to Detect Hotspots," Mar. 2004, Advantage.
Cantronic Systems (Canada) Inc., "Detecting Wildfire with Infrared Imaging".
Honeywell, 2018 Product Guide Americas, "Industrial Fixed Flame Detection," Feb. 2018, 1V0, Americas.
Det-Tronics, "Sulfur Flame Detection," 77-1022-3.0, Oct. 2015, Minneapolis, MN.
Alberta, "Ambient Air Monitoring Performance Specification Standards—Continuous Analyzers," Dec. 16, 2015.
Alberta Health Services, "Acute Exposure Health Effects of Hydrogen Sulphide and Sulphur Dioxide," Jun. 2012.
Geoff Wilcox, "Evaluation of Portable Gas Monitors for the Detection of Low Levels of H2S and SO2 in Petroleum Environments," BP Hull Research & Technology Centre, UK.
National Academies, "Health Effects of Project Shad Chemical Agent: Sulfur Dioxide," 2004, The Center for Research Information, Inc.
Dr. Min Chen, "Pipeline Leak Detection System at Chuandongbei Project," Nov. 15, 2017, Unocal East China Sea, Ltd.
Kai Yang et al., "Direct Retrieval of Sulfur Dioxide Amount and Altitude from Spaceborne Hyperspectral UV Measurements: Theory and Application," Journal of Geophysical Research, vol. 115, D00L09, doi:10.1029/2010JD013982, 2010.
Thomas Charles Wilkes et al., "A Low-Cost Smartphone Sensor-Based UV Camera for Volcanic SO2 Emission Measurements," Remote Sens. 2017, 9, 27, MDPI, Basel, Switzerland.
A.J. Prata, "Measuring SO2 Ship Emissions with an Ultraviolet Imaging Camera," Atmos. Meas. Tech., 7, 1213-1229, 2014, Copernicus Publications.
Simon A. Carn et al., "NASA Satellites Track Air Pollution from Sulfur Fires in Iraq," Oct. 21, 2016, Michigan Technological University.
State of Alaska Department of Environmental Conservation, "Standard Operating Procedures for Sulfur Dioxide (SO2) Monitoring by Ultraviolet Fluorescence," Feb. 2012, Revision 2, Anchorage, AK.
S. A. Carn, "Sulfur Dioxide Emissions from Peruvian Copper Smelters Detected the Ozone Monitoring Instrument," May 1, 2007, Geophysical Research Letters, vol. 34, L09801, doi: 10.1029/2006GL029020.
Simon A. Carn et al., "Tracking Volcanic Sulfur Dioxide Clouds for Aviation Hazard Mitigation," Feb. 21, 2008, Nat Hazards, DOI 10.1007/S11069-008-9228-4.
Cerex Monitoring Solutions, Inc., "UV Sentry, Open Path Multi-Gas Uvdoas Analyzer".
Dmitry S. Efremenko et al., "Volcanic SO2 Plume Height Retrieval from UV Sensors Using a Full-Physics Inverse Learning Machine Algorithm," Aug. 22, 2017, Informa UK Limited.
V. E. Fioletov et al., "Application of OMI, SCIAMACHY, AND GOME-2 Satellite SO2 Retrievals for Detection of Large Emission Sources," Oct. 4, 2013, Journal of Geophysical Research: Atomospheres, vol. 118, 11, 399-11,418, doi: 10.1002/jgrd.50826.
A.J. Krueger et al., "Volcanic Sulfur Dioxide Measurements from the Total Ozone Mapping Spectrometer Instrucments," Jul. 20, 1995, Journal of Geophysical Research, vol. 100, No. D7, pp. 14,0457-14,076.
Lori Mandable, "Source Detection of SO2 Emissions with Unknown Origins Using UV Remote Sensing and Numerical," 2013, George Mason University, Fairfax, VA.
Stephen A. Marino, "Operation and Calibration of the NPS Ultraviolet Imaging Spectrometer (NUVIS) in the Detection of Sulfur Dioxide Plumes," Dec. 1999, Naval Postgraduate School, Monterey, CA.
Toshiya Mori et al., "Sulfur Dioxide Emissions during the 2011 Eruption of Sinmoedake Volcano, Japan," Jul. 8, 2013, Earth Planets Space, 65, 573-580.
Helen Amanda Fricker, "Lecture 11: Passive Microwave Remote Sensing," visited Nov. 7, 2019 at https://topex.ucsd.edu/rs/Lec11.pdf.
Christian M. Ho. et al., "Estimation of Microwave Power Margin Losses Due to Earth's Atmosphere and Weather in the Frequency Range of 3-30 GHz," Jan. 20, 2004, Jet Propulsion Laboratory.
Christian Ho et al., "Atmospheric Noise Temperature Induced by Clouds and Other Weather Phenomena at SHF Band (1-45 GHz)," Aug. 11, 2005, Jet Propulsion Laboratory, Pasadena, CA.
Honeywell, "Dielectric Constant Table," visited Nov. 7, 2019 at https www.honeywellprocess.com library marketing tech-specs Dielectric Constant Table.
boulderest.com, "Best Portfolio," visited Nov. 7, 2019 at https://boulderest.com/portfolio.html.
Airborne Sensors, "HyMAS (Hyperspectral Microwave Atmospheric Sounder) / Airborne Instrument," visited Oct. 2, 2019 at https://eoportal.org/web/epoortal/airborne-sensors/content/-/article/hymas.
William J. Backwell et al., "All-Weather Hyperspectral Atmospheric Sounding," Nov. 2, 2010, Lincoln Laboratory Journal.
L.M. Hilliard et al., "Hyperspectral Microwave Atmospheric Sounder (HyMAS) Architecture and Design Accommodations," visited Nov. 7, 2019 at https://ntrs.nasa.gov/search.jsp?R=20130011065 2019-10-02T17:37:22+00:00Z.
W.F. Kolbe, "Absorption Coefficients of Sulfur Dioxide Microwave Rotational Lines," Mar. 10, 1975, Lawrence Berkeley National Laboratory.
Shady H. Suleiman et al., "Laboratory Measurement of the Temperature Dependence of Gaseous Sulfur Dioxide (SO2) Microwave Absorption with Application to the Venus Atmosphere," Feb. 25, 1996, Journal of Geophysical Research, vol. 101, No. E2, pp. 4623-4635.
Vivienne H. Payne et al., "Water Vapor Continuum Absorption in the Microwave," Jun. 2011, IEEE Transactions on Geoscience and Remote Sensing, vol. 49, No. 6.
W.D. Philpot, "Remote Sensing Fundamentals, Passive Microwave Sensing," 2012, Cornell University.
V. Melnikov et al., "Radar Polarimetric Signatures of Fire Plumes".
Pierre-Marie Robitaille, "On the Eart Microwave Background: Absorption and Scattering by the Atmosphere," Jul. 2007, vol. 3, Department of Radiology, The Ohio State University, Columbus, OH.
Unknown, "Passive Microwave Systems," Rees Chapter 7.
Aerodyne Research, Inc., "Single Laser Trace Gas Monitors: The Mini Monitor," Billerica, MA.
Block Engineering, "Large Area Open Path Chemical Detection," Southborough, MA.

(56) References Cited

OTHER PUBLICATIONS

Andrea Gabrieli, "Remote Measurements of Volcanic Gases Using Thermal Infrared Hyperspectral Imaging," Apr. 2018.
Joy Crisp, "NASA EOS IDS Volcanology," visited Oct. 2, 2019 at http://eos.higp.hawaii.edu/.
M. Kastek et al., "Passive Optoelectronics Systems for Standoff Gas Detection: Results of the Test," 2015, WIT Transactions on Ecology and the Environment, vol. 198.
Peter Louie, "Application of UAV Based Sensor Technology for Ship Emission Monitoring and High Sulfur Fuel Screening in Hong Kong," Jun. 26-27, 2018, Hong Kong University of Science and Technology.
Jet Propulsion Laboratory, "NASA's AIRS Displays Sulfur Dioxide Plumes After Raikoke Eruption," visited Oct. 1, 2019 at https://www.jpl.nasa.gov/spaceimages/details.php?id=PIA23421.
A. J. Prata et al., "Retrieval of Sulfur Dioxide from a Ground-Based Thermal Infrared Imaging Camera," Sep. 3, 2014, Atmospheric Measurement Techniques.
Fred Prata, "Retrieval of SO2 from High Spectral Resolution Measurements: AIRS and IASI," Apr. 14, 2010, ITSC-17 Monterey, CA.
Youwen Sun et al., "Industrial SO2 Emission Monitoring through a Portable Multichannel Gas Analyzer with an Optimized Retrieval Algorithm," Mar. 21, 2016, Atmospheric Measurement Techniques.
Telops, "Volcanic Eruption Observations from an Elevated Point of Stromboli Using Thermal Hyperspectral Imaging," 2017, Québec, QC Canada.
Amanda Berg, "Detection and Tracking in Thermal Infrared Imagery," 2016, Linköping University.
DLR & INGV, "Temperature Emissivity Signatures for Geosphere and Pedosphere".
M. Höpfner et al., "Sulfur Dioxide (SO2) from MIPAS in the Upper Troposphere and Lower Stratosphere 2002-2012," Jun. 29, 2015, Atmospheric Chemistry and Physics.
Earthdata NASA, "User Profile: Dr. Mike Ramsey, Who Uses NASA Earth Science Data?", visited Oct. 3, 2019 at https://earthdata.nasa.gov/learn/user-resources/who-uses-nasa-earth-science-data-user-profile-dr-mike-ramsey.
NASA, "Sulfur Dioxide" visited Nov. 7, 2019 at https eospso.gsfc.nasa.gov sites default files publications SO2poster_508.
I. M. Watson et al., "Thermal Infrared Remote Sensing of Volcanic Emissions Using the Moderate Resolution Imaging Spectroradiometer," Journal of Volcanology and Geothermal Research 135 (2004) 75-89, Elsevier B.V.
Joseph A. Shaw et al., "Physics Principles in Radiometric Infrared Imaging of Clouds in the Atmosphere," Oct. 22, 2013, IOP Publishing, European Journal of Physics.
V. Kovalev, "Determination of the Smoke-Plume Heights and their Dynamics with Ground-Based Scanning Lidar," Mar. 6, 2015, vol. 54, No. 8, Applied Optics.
James O. Thompson, "MMT-Cam: A New Miniature Multispectral Thermal Infrared Camera System for Capturing Dynamic Earth Processes," IEEE Transactions on Geoscience and Remote Sensing.
Vincent J. Realmuto et al., "Impact of Atmospheric Water Vapor on the Thermal Infrared Remote Sensing of Volcanic Sulfur Dioxide Emissions: A Case Study from the Pu'u 'O'o Vent of Kilauea Volcano, Hawaii," Sep. 10, 2000, Journal of Geophysical Research, vol. 105, No. B9, pp. 21, 497-21, 508.
Joseph A. Shaw et al., "Radiometric Cloud Imaging with an Uncooled Microbolometer Thermal Infrared Camera," Article in Optics Express, Aug. 2005.
N. Von Wahl et al., "An Integrated Approach for Early Forest Fire Detection and Verification Using Optical Smoke, Gas and Microwave Sensors," WIT Transactions on Ecology and the Environment, vol. 137.
Nachappa Gopalsami et al., "The Use of Microwave Radar for Remote Detection of Gas Pipeline Leaks," Research Gate.
Wolfgang Krüll et al., "2012 International Symposium on Safety Science and Technology Early Forest Fire Detection and Verification Using Optical Smoke, Gas and Microwave Sensors," Procedia Engineering 45 (2012) 584-594.
Paul G. Steffes, "Microwave Remote Sensing of Planetary Atmospheres: From Staelin and Barrett to the Nasa Juno Mission," Aug. 2008, Research Gate.
Paul G. Steffes, "Laboratory Measurements of the 3.7-20 cm Wavelength Opacity of Sulfur Dioxide and Carbon Dioxide under Simulated Conditions for the Deep Atmosphere of Venus," Icarus 245 (2015) 153-161.

* cited by examiner

METHOD AND APPARATUS FOR SULFUR FIRE-WATCH AND DETECTION

CROSS-REFERENCE TO RELATED APPLICATION

This application claims priority to U.S. Provisional Patent Application 62/760,505 filed on Nov. 13, 2018. The above referenced application is incorporated by reference in its entirety.

FIELD OF THE INVENTION

This disclosure relates to a method and apparatus for detecting and measuring sulfur fires.

BACKGROUND

Typical sulfur storage sites contain large amounts of sulfur that may be stored in large blocks, pellets, or granule form. Some sulfur may be stored in large stockpiles either outdoors or within warehouses, where the stockpiles may have a size that could be over 30 meters (98 feet) high and approximately 300 meters (984 feet) long and approximately 200 meters (656 feet) wide. In fact, some of the sulfur facilities may have an area of greater than 0.25 square kilometers (0.096 sq. miles). One of the bigger dangers at these storage sites is the risk of fire, as sulfur is combustible and when burned gives off a toxic gas, sulfur dioxide ($SO_2$), which is an irritant to a person's lungs in low concentrations and could be toxic or life threatening the concentrations are high. Thus, any fire detection system would help a storage site comply with appropriate safety regulations set forth by Occupational Safety and Health Administration (OSHA) or The National Institute for Occupational Safety and Health (NIOSH). Sulfur dioxide also poses an environmental threat as being a contributor to acid rain.

When sulfur burns it typically has a bluish or violet colored flame, which can be missed by the human eye in the visible light spectrum. In addition, sulfur dioxide is a colorless gas that can also be missed by the human eye making its detection difficult. Further, since sulfur burns at a temperature lower than wood or hydrocarbons, a sulfur fire may not be easily detected. At present, sulfur fire-watch and detection is done by a person who is physically on site, where he or she may detect a sulfur fire by the distinct smell given off by the sulfur dioxide.

BRIEF SUMMARY

The following presents a general summary of aspects of the disclosure in order to provide a basic understanding of the disclosure. This summary is not an extensive overview of the disclosure. It is not intended to identify key or critical elements of the disclosure or to delineate the scope of the disclosure. The following summary merely presents some concepts of the disclosure in a general form as a prelude to the more detailed description provided below.

Aspects of this disclosure may relate to a system for detecting sulfur fires in a sulfur stockpile that include a sensor located a predetermined distance from the sulfur stockpile, wherein the sensor may have a field of view of the sulfur stockpile. The sensor may be configured to receive radiation emitted from the sulfur stockpile. The system may also include a processor configured to receive data from the sensor, and where upon receiving data from the sensor, the processor may determine if an amount of sulfur dioxide gas is greater than a predetermined limit of sulfur dioxide gas. If the processor determines the amount of sulfur dioxide gas is greater than the predetermined limit, the processor may send a signal to an alarm. The sensor may be capable of receiving electromagnetic radiation within a range of 1 µm wavelength and 16 µm. In some embodiments, the sensor may be an infrared sensor. The predetermined limit of the amount of sulfur dioxide gas may be a slant column density of a sulfur plume with a path concentration above about 1,000 ppm-m. In addition, the predetermined distance from the sulfur stockpile may be within 5000 meters (3.1 miles) of the sulfur stockpile. In some instances, the sensor may actually comprise three sensors evenly spaced apart from each other around the sulfur stockpile. The sensor may also be configured to move the field of view of the sensor in a predetermined scan schedule, where the predetermined scan schedule may be a range height indicator scan using a fixed azimuth angle while varying an elevation angle. Additionally, the system may transmit the signal wirelessly to a remote computer. In other embodiments, the sensor may be a microwave sensor. For instance, the sensor may be an active microwave sensor, where the active microwave sensor detects radiation that is emitted by the sulfur stockpile and other objects within the field of view, or the sensor may be a passive sensor, where the passive microwave sensor detects radiation that is emitted or reflected by the sulfur stockpile and other objects within the field of view.

Still other aspects of this disclosure may relate to a system for detecting sulfur fires in a sulfur stockpile that include an infrared sensor located a predetermined distance from the sulfur stockpile, where the infrared sensor has a field of view of the sulfur stockpile and is configured to receive radiation emitted from the sulfur stockpile. The system may also include a processor configured to receive data from the infrared sensor, and a non-transitory, computer-readable medium storing computer-executable instructions that, when executed by the processor, causes the processor to at least: (1) receive data from the infrared sensor; (2) determine using thermal contrast imaging if sulfur dioxide is present in the field of view; (3) calculate a slant column density of a sulfur plume; (4) compare the calculated slant column density to a predetermined limit; and (5) send a signal to an alarm if the calculated slant column density is greater than a predetermined limit of sulfur dioxide gas. The system may have a predetermined limit of sulfur dioxide gas is at a path concentration above about 1,000 ppm-m, and the system may be set at a predetermined distance from the sulfur stockpile is within 5000 meters (3.1 miles) of the sulfur stockpile. In addition, the sensor may be three sensors that are evenly spaced apart from each other around the sulfur stockpile. The sensor may be connected to a mount that is configured to move the sensor such that the field of view of the sensor moves in a predetermined scan schedule.

Yet other aspects of this disclosure may relate to a system for detecting sulfur fires in a sulfur stockpile an infrared sensor located a predetermined distance from the sulfur stockpile, where the infrared sensor has a field of view of the sulfur stockpile and is configured to receive radiation emitted from the sulfur stockpile. The system may also include a processor configured to receive data from the infrared sensor and a non-transitory, computer-readable medium storing computer-executable instructions that, when executed by the processor, causes the processor to at least: (1) receive data from the infrared sensor; (2) determine a stockpile temperature of a portion of the sulfur stockpile within the field of view; (3) compare the stockpile temperature to a predetermined threshold temperature, where upon determining that the stockpile temperature is greater than the predetermined threshold temperature, send a signal to an alarm. The predetermined threshold temperature may be 190° Celsius. The system may further include a plurality of infrared sensors is evenly spaced apart around the sulfur stockpile.

DETAILED DESCRIPTION

In the following description of various example structures according to the disclosure, reference is made to the accompanying drawings, which form a part hereof, and in which are shown by way of illustration various example devices, systems, and environments in which aspects of the disclosure may be practiced. It is to be understood that other specific arrangements of parts, example devices, systems, and environments may be utilized and structural and functional modifications may be made without departing from the scope of the present disclosure. Nothing in this specification should be construed as requiring a specific three-dimensional orientation of structures in order to fall within the scope of this disclosure. The reader is advised that the attached drawings are not necessarily drawn to scale.

Generally, this disclosure relates to a method and system for automating sulfur fire-watch and sulfur fire detection. Thermal infrared remote sensing technologies may be used for the detection of emission plumes of atmospheric sulfur dioxide gas in different environmental conditions that can provide data to determine the source of the plume. In more detail, the sulfur fire-watch and detection system 100 may comprise a remote ground-based, airborne, or space-borne infrared sensor 102, with a thermal infrared imaging system that can detect sulfur dioxide gas to provide for unsupervised remote day and nighttime sulfur fire-watch, hot spot detection, early sulfur fire prevention, sulfur fire detection, and/or sulfur fire control of unattended combustible sulfur blocks, sulfur stockpiles, sulfur plants, or equipment using remote sensing devices that includes detection, measurement, and analysis of electromagnetic radiation to determine the presence of sulfur dioxide gas. The system 100 uses a source of electromagnetic radiation as electromagnetic radiation may penetrate through the atmosphere, where the system 100 may measure and analyze the electromagnetic radiation, digitize the analysis, transmit the data, and signal an alarm if a harmful condition is detected. In some embodiments, the system 100 may be ground-based such as being mounted on a platform attached to the ground within a fixed distance from the Earth's surface. However, in some instances, infrared sensors may be mounted to an airborne system, like a drone or other aircraft, or in some cases asatellite, to monitor known sulfur stockpile locations to detect sulfur dioxide gas.

Figure 1:
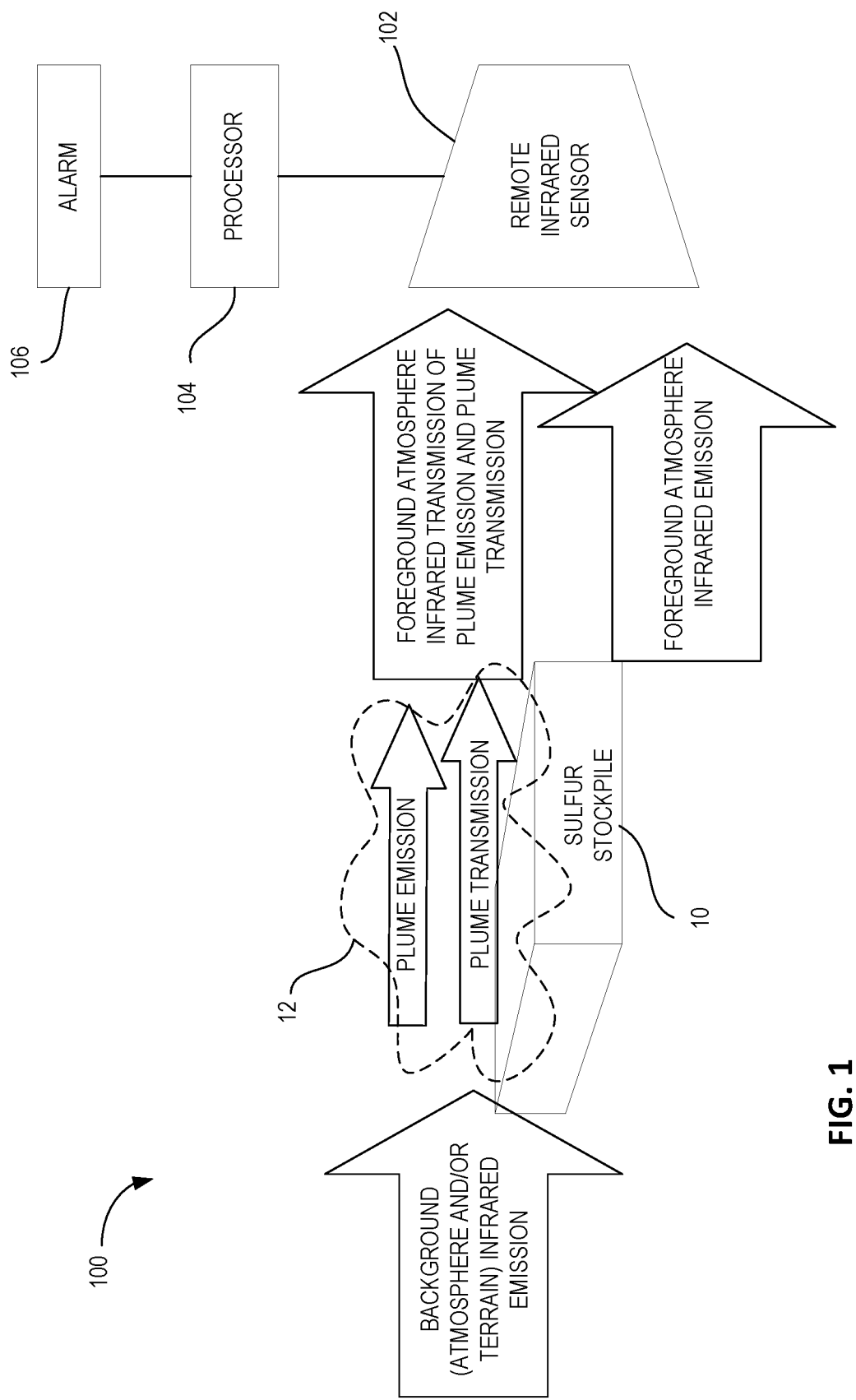
FIG. 1 is a schematic view of a system for detecting sulfur fires as disclosed herein.

FIG. 1 illustrates a schematic of an exemplary sulfur fire detection system 100 for remotely detecting a sulfur fire in a sulfur stockpile 10, where the sulfur stockpile 10 may be an unattended sulfur block(s), a pile(s) of sulfur pellets or granules, a sulfur plant(s), sulfur processing equipment, or other large quantity of sulfur. The fire detection system 100 may comprise a remote infrared sensor 102 or a plurality of remote infrared sensors 102 that is/are positioned a predetermined distance away from the sulfur stockpile 10, but may have a generally uninterrupted field of view of the sulfur stockpile 10. The infrared sensor 102 may be able to operate during both daytime and nighttime to enable fire-watch control at all times. Infrared sensors may be preferred over a passive type ultraviolet (UV) sensor, as a UV sensor may not effectively function on a 24 hour basis since UV radiation is limited at nighttime. Generally, the infrared sensor 102 may receive the electromagnetic radiation emitted from the background atmosphere or terrain located behind the sulfur stockpile 10, radiation emitted from the sulfur stockpile 10 within the storage area, radiation emitted from the foreground atmosphere and terrain, which is located between the sensor 102 and the sulfur stockpile 10, and any radiation emitted from a sulfur fire or sulfur plume 12 if present. As disclosed herein, the background terrain may encompass all of the possible land-based radiation sources, such as the land itself, any buildings, or sulfur plant equipment that are present within the field of view of the sensor 102. The sensor 102 may include or be connected to a processor 104 that may convert the radiation received by the sensor 102 to an electronic signal that may be processed into numerical or image data. The data may then be further processed to detect the presence of sulfur dioxide gas ($SO_2$) within the atmosphere captured in its field of view using thermal contrast imaging to determine the thermal contrast between the background and sulfur dioxide gas. If the processor 104 determines the presence of sulfur dioxide gas, the processor 104 may send a signal to an alarm 106 that is able to communicate via an audible alert, a visual alert, or some other definitive communication that a sulfur fire may be present. The alarm 106 may alert any emergency personnel or responders to take the appropriate actions to address the situation, including extinguishing the fire.

As discussed above, when a sulfur fire is not present, the sensor 102 may receive electromagnetic radiation emitted from the background atmosphere or terrain, located behind the sulfur dioxide plume 12, radiation emitted from the sulfur stockpile 10 within the storage area, and radiation emitted from the foreground atmosphere and terrain, which is located between the sensor 102 and the sulfur stockpile 10. When a sulfur fire is present, the sensor 102 may receive additional radiation emitted by the sulfur fire. In addition, when a sulfur fire is present, radiation emitted from the background atmosphere or terrain located behind the sulfur stockpile 10 may be absorbed at certain wavelengths such that the radiation emitted by the background atmosphere and terrain is altered as the radiation moves through a sulfur dioxide plume 12 created by the sulfur fire such that the sensor 102 receives only the background radiation able to be transmitted through the sulfur dioxide plume 12. One or more sulfur dioxide bands or absorption features may be used for sensing sulfur dioxide. As a result, a good balance between sensitivity and measurement range may be obtained. For example, as known to one skilled in the art, sulfur dioxide has an apparent wavelength absorption feature at approximately 8.6 micrometer (μm) electromagnetic wavelength. Thus, if the processor 104 determines that a reduction in radiation around the 8.6 μm wavelength, or within a range of 8 μm and 9 μm, when compared to the background and foreground atmosphere and terrain, a high probability of the presence of sulfur dioxide exists, and therefore a high probability of a sulfur fire exists. In some embodiments, other sulfur dioxide absorption features may be used to sense sulfur dioxide. The atmosphere may consist of many other infrared-absorbing gases, such as water vapor, carbon dioxide, nitrous oxide, carbon monoxide, nitric oxide, nitrogen dioxide, and methane. The absorption features of these gases may interfere with one another, and have significant cross interferences that must be considered to measure sulfur dioxide emission with greatest accuracy. These methods may require additional information and filtering. For instance, sulfur dioxide has a relatively strong absorption band at a wavelength of approximately 7.3 µm, but water vapor also has an overlapping absorption band near this same wavelength. Therefore, to determine the presence of sulfur dioxide, the amount of water vapor (relative humidity) in the atmosphere must be known and filtered out of the results to determine the presence and amount of sulfur dioxide gas. As another option, water vapor concentration tends to be greatest near ground-level and reduces exponentially with altitude up to a height of approximately 3,000 meters (1.86 miles). When air is sufficiently dry in the path along the sensor's field of view, such that water concentration does not excessively obscure the approximate 7.3 µm wavelength sulfur dioxide absorption feature, then a wavelength that indicates water vapor is present may be used, such as the water vapor absorption band at wavelength of approximately 2.6 µm, to determine the atmosphere's watervapor slant column density that may be used to automatically calibrate or correct the approximate 7.3 µm sulfur dioxide wavelength measurement to account for any water vapor interference at that wavelength. Still another option may comprise analyzing the received data from the sensor 102 at a wavelength that is known to have no significant absorption of sulfur dioxide and no significant absorption of interference gases to use as a baseline to automatically calibrate or correct the sulfur dioxide detection/determination. Accordingly, the apparent wavelength absorption feature at approximately 8.6 µm has significantly less overlap with other atmospheric gases, so this wavelength may be preferable, but sulfur dioxide gas may be detected by analyzing other wavelengths.

The sensor 102 may operate in the infrared spectrum with a possible spectral range between 5 µm wavelength and 14 µm wavelength and may be a cooled or uncooled sensor as known to one skilled in the art. In some embodiments, the sensor 102 may operate in a spectral range of 1 µm wavelength and 16 µm wavelength. This range may cover multiple absorption wavelengths that may be analyzed using a multichannel algorithm as known to one skilled in the art. A cooled sensor may be cryogenically cooled and offer less internal temperature fluctuation, less noise or less error, or better sensitivity or image resolution compared to the image resolution of an uncooled sensor. The uncooled sensor, while having lower resolution, may offer advantages of an easier setup, improved reliability, and lower initial cost as well as lower operating costs.

Once the presence of sulfur dioxide gas is determined, the slant column densities of the sulfur dioxide may be quantified. In some cases, hydrogen sulfide ($H_2S$) may not be sensed or targeted. As hydrogen sulfide may be approximately 50 times less absorbing than sulfur dioxide in the mid-infrared spectrum. In large quantities, hydrogen sulfide may be detected. However, sulfur owners may not want hydrogen sulfide targeted as some sulfur includes hydrogen sulfide. The infrared sensor 102 may be located a predetermined distance away from the sulfur stockpile 10. Depending on the resolution of the sensor 102, this predetermined distance may be as much as 17 kilometers (10.6 miles) away in order to quantify slant column densities. In other embodiments, the sensor 102 may be remotely positioned at a distance within a distance of 5000 meters from the sulfur stockpile 10 and/or a detectable plume 12. Additionally, in some embodiments, the sensor 102 may include a plurality of sensors 102 positioned in locations around the sulfur stockpile 10 such that the field of view of the combined array of sensors 102 can encompass the entire sulfur stockpile 10. For instance, to improve quantitative measurements of the sulfur dioxide plumes 12, three sensors 102 may be evenly spaced around the stockpile 10 approximately 120-degrees apart from each other. In some cases, a large field of view may be necessary, as the sulfur dioxide plume 12 may be buoyant near the fire, so the plume 12 may rise, and then may cool to be denser than the surrounding air, so the plume 12 may sink around the sulfur stockpile 10, and remain relatively stagnant, or be moved by any atmospheric conditions such as wind. The sensor 102 may further be set up to have a fixed field of view or set up to have a scanning field of view such that the sensor is rotated to increase the overall field of view. For instance, the sensor 102 may be configured to rotate to move the field of view of the sensor 102 to sweep across the sulfur stockpile 10 to scan for sulfur dioxide over a larger area at a predetermined scan schedule. As a non-limiting example, the sensor 102 may be connected to a mount that is able to move the sensor 102 through a predetermined scan schedule as the mount may be configured to rotate to adjust both the azimuth and elevation angle of the sensor as well as adjust the height that the sensor is positioned. The mount may rigidly attach to a platform, where the platform may be rotated or controlled using a plurality of electromechanical servomotors or other means known to one skilled in the art. The scan schedule may include a Range Height Indicator (RHI) scan using a fixed azimuth angle while varying an elevation angle to obtain a vertical cross-section through the atmosphere. The scan schedule may also include a Plan Position Indicator (PPI) scan using a fixed elevation angle, while varying azimuth angle to get nearly horizontal cross sections of the atmosphere. In addition, the field of view of the sensor 102 may encompass a portion of the background behind the sulfur stockpile 10 such that the sensor 102 may be located on the ground (i.e. where the platform may have a height within 50 meters (164 feet) from the ground). For example, if the sulfur stockpile 10 is 30 meters (98.4 feet) high, the sensor 102 may be mounted higher than the top surface (or total height) of the sulfur stockpile 10. The sensor 102 may have a field of view pointing generally horizontal or pointing downwards (i.e. a negative acute elevation angle relative to a horizontal plane) where the sky/atmosphere or region behind the sulfur stockpile 10 is within the field of view of the sensor 102 from above the stockpile. Alternatively, the sensor 102 may have a field of view pointing generally upward (i.e. a positive acute elevation angle relative to a horizontal plane) where the sky/atmosphere or region behind the sulfur stockpile 10 is within the field of view. As another option, the sensor 102 may be fitted with a lens or other optical device to increase the field of view to enable to sensor to detect the presence of sulfur dioxide over a larger area. The sensor 102 may further include shielding from any extraneous electromagnetic radiation. By incorporating some amount of the background into the field of view, the thermal contrast between the background and any sulfur dioxide may be more evident. As another option, a radiation may be emitted by the sensor 102 in the direction of the target to be investigated or the sulfur stockpile 10 may be illuminated with electromagnetic radiation from infrared LED lighting to make the sulfur dioxide plume 12 easier to detect.

The processor 104 may be utilized to process data received from the sensor 102. The processor 104 may be a general-purpose processor, a digital signal processor (DSP), an application-specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, or any conventional processor, controller, microcontroller, or state machine. The processor 104 may also be implemented as a combination of computing devices, e.g., a combination of a DSP and a microprocessor, a plurality of microprocessors, one or more microprocessors in conjunction with a DSP core, or any other such configuration. The one or more implementations described throughout this disclosure may utilize logical blocks, modules, and circuits that may be implemented or performed with a processor.

The processor 104 may be used to implement various aspects and features described herein. As such, the processor 104 may be configured to perform any desired operation on one or more data streams received from the sensor 102. Further, it will be appreciated that the processor 104 may execute multiple calculations, in parallel or serial, at a very high throughput frequency using the received data from the sensor 102 to determine the presence of sulfur dioxide gas and communicate the any desired outputs. As such, the processor 104 may be configured to execute hundreds of thousands, millions, or billions or more calculations per second. The processor 104 may include a processing unit, input/output (I/O), or system memory to store and execute software instructions. The I/O may include a microphone, keypad, touch screen, and/or stylus through which a user of the processor 104 may provide input, and may also include one or more of a speaker for providing audio output or a video display device for providing textual, audiovisual and/or graphical output. The system memory may include data storage capabilities, such as USB and other forms of similar data storage capabilities. The processor 104 may be programmed to include data logging features as well and to record and log any and all data from the processor 104 and the sulfur fire detection system 100. The data logged may then be uploaded to be analyzed and reviewed as needed and required.

Additionally, the sulfur fire detection system 100 may include a remote communication method, such as Bluetooth, wireless, or a radio communication as known to one skilled in the art. The purpose of the remote communication is to transmit data from the processor 104 and the sulfur fire detection system 100 to any remote locations as required. Additionally, the Bluetooth or other wireless communication methods may enable communication from the sulfur fire detection system 100 to a smart device, such as a mobile phone or remote computer.

Figure 2:
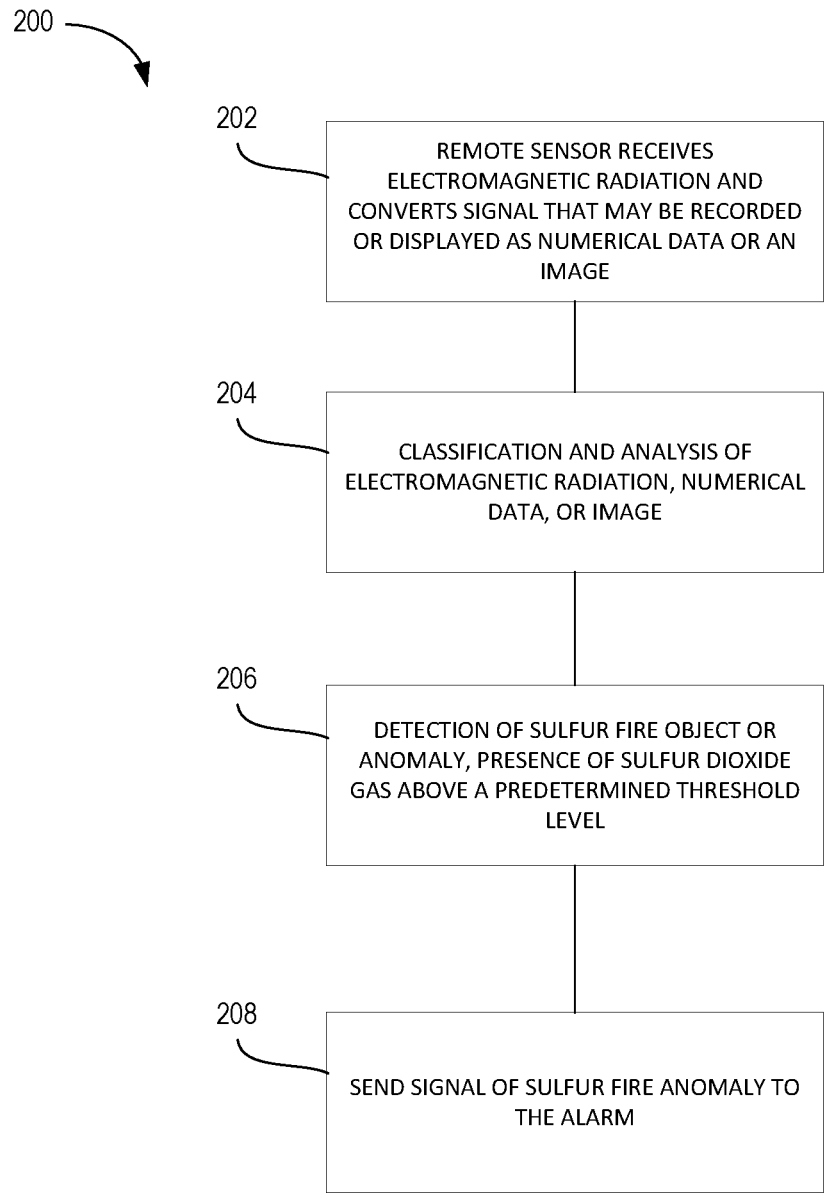
FIG. 2 is a flowchart of a method for detecting sulfur fires as disclosed herein.

FIG. 2 illustrates an exemplary flow chart of the process for determining the presence of a sulfur anomaly or fire (200). As shown and discussed above, the sensor 102 may receive electromagnetic radiation from both the background objects, the sulfur stockpile 10, the foreground, and from the sulfur dioxide plume 12 if a fire is present. The plume 12 may also reflect radiation from solar, foreground atmosphere or terrain, and may also absorb or reflect radiation emitted by an active sensor, or emitted by an auxiliary source, as an option. The sensor 102 may process that data into a signal that can be converted into numerical or image data (202). The processor 104 may then analyze that signal via thermal contrast imaging, primarily in the infrared spectrum, to determine if sulfur dioxide gas ($SO_2$) is present (204). If the presence of sulfur dioxide gas over a predetermined threshold is detected (206), the processor 104 then sends a signal to the alarm 106 of a possible sulfur fire (208). As another option, processor 104 may identify and discriminate a sulfur dioxide plume and output classification or location. As still another option, the processor 104 may quantify the sulfur dioxide slant column density and output the sulfur dioxide slant column density or concentration isopleths showing areas of minimum to high concentrations that illustrate the highest health risk. Remote sensing may be useful in determining protective actions for the public and responders, as concentrations above 1,000 ppm may be fatal within 10 minutes. If air containing 20.95% oxygen is used for sulfur combustion, then a sulfur dioxide concentration of approximately 20.5% can theoretically be achieved at the fire source. The upper practical limit for industrial production of sulfur dioxide gas is about 18% (180,000 ppm). Remote sensing system's processor 104 for example may output a signal to the alarm 106 if it determines that sulfur dioxide is present or if the sulfur dioxide is at or above at a predetermined slant column density above about 2E+17 sulfur dioxide molecules per square centimeter (molecules/$cm^2$), or alternatively at or above a path concentration above about 1,000 ppm-m, or optionally above about 0.1% (1,000 ppm) along a 1 meter path distance or above about 1 ppm along a 1,000 meter path distance, as may be classified as evidence of a hot spot or sulfur fire, for remote fire-watch. The lower detection limit is a function of the actual sensor's construction and actual conditions on site, which for a ground-based uncooled infrared remote sensor may be a slant column density down to approximately 0.001 grams sulfur dioxide per square meter ($g/m^2$), when the sensor 102 is located approximately 17 kilometers (10.6 miles) from distant plume. However, slant column density error may be approximately plus and minus 0.2 grams sulfur dioxide per square meter ($g/m^2$), which may limit practical lower values of sulfur dioxide measurement, or the sulfur dioxide determination for some instruments, under favorable conditions, with no clouds and sensor located approximately 2 kilometers (1.2 miles) from a sulfur plume. As another option, the slant column density values may be output with errors of approximately 10%, or 20% depending on actual remote sensor configuration, depending upon sensor resolution and the quantity retrieval algorithm. As a further option, average mass flow emission rate of sulfur dioxide may be estimated, which may include an estimate of plume velocity by tracking features in the plume.

As another option, once the processor 104 has determined that a sulfur fire may be present through analysis for sulfur dioxide gas, a secondary process may be utilized to determine the relative temperatures of the objects within the thermal image or data created from the received electromagnetic radiation. The theoretical combustion temperature for production of sulfur dioxide gas using dry air at 60 to 80° Celsius (140° F. to 176° F.) and (dry) liquid sulfur at 140° Celsius (284° F.) is about 1000° Celsius (1832° F.) at sulfur dioxide production concentration of 10%, increasing to about 1600° Celsius (2912° F.) at sulfur dioxide production concentration of about 18%. In this secondary process, the processor 104 may compare the relative temperatures of a portion of the stockpile 10 or the analyzed line-of-sight objects to verify that a temperature of sulfur stockpile 10 surface is above a threshold temperature. As an example, the threshold temperature may be a temperature greater than 190° Celsius (374° F.). If the processor 104 determines the temperature of the sulfur stockpile 10 or the analyzed line-of-sight objects is greater than the threshold temperature, the processor 104 may confirm the presence of the sulfur fire by signaling a second alarm. In some embodiments, the processor 104 may only send the signal to the alarm 106 once both the presence of sulfur dioxide gas is detected to be over the predetermined limit and the temperature of objects in the field of view is determined to by over the threshold temperature.

As another option to confirm the detection of a sulfur fire, a passive microwave sensor may be used alone or in conjunction with the infrared sensor 102 to determine the temperature at a remote distance. As known to one skilled in the art, a microwave sensor may be configured to acquire data and operate in a microwave range of the electromagnetic spectrum of approximately 0.3 GHz and 35 GHz (wavelength of 100 cm (39.4 in.) and 0.86 cm (0.34 in)). By analyzing the data received from the microwave sensor, the processor 104 may be used to detect a hot spot (or region of elevated temperature) in the sulfur block to confirm the infrared sensor's detection of sulfur dioxide gas. The microwave sensor may have advantages over the infrared sensor in that it may operate in low visibility or partially obstructed line of sight of the sensor as the microwaves may penetrate through smoke or other atmospheric elements where the infrared may be absorbed or adversely affected at those wavelengths.

In addition, when the processor 104 determines that a portion of the stockpile 10 is above the threshold temperature, the processor 104 may further determine an approximate location of the sulfur fire/hot spot within the field of view and communicate this location to a remote computer, mobile device, or other receiver to assist responding personnel to assist with the fire. The system 100 may also operate at a sampling rate such that the processor 104 acquires data from the sensor 102 at fixed time intervals so the processor 104 may compare data from a first time, To, to a second time taken later, Ti. By comparing images at different time intervals, the system 100 may recognize changes and possibly alert responding personnel to potential sulfur fires. In some embodiments, the predetermined time intervals may be an image/data is being received and transmitted every 3 to 5 minutes, or in some cases the images between 15 minute intervals may be compared. Alternatively, the images and data may be updated and received multiple times a minute. As another alternative, imaging frame rates may be up to approximately 60 Hz and can be combined with a necessary data transfer rate, enabling fire-watch system to operate at up to approximately one cycle per second.

Figure 3:
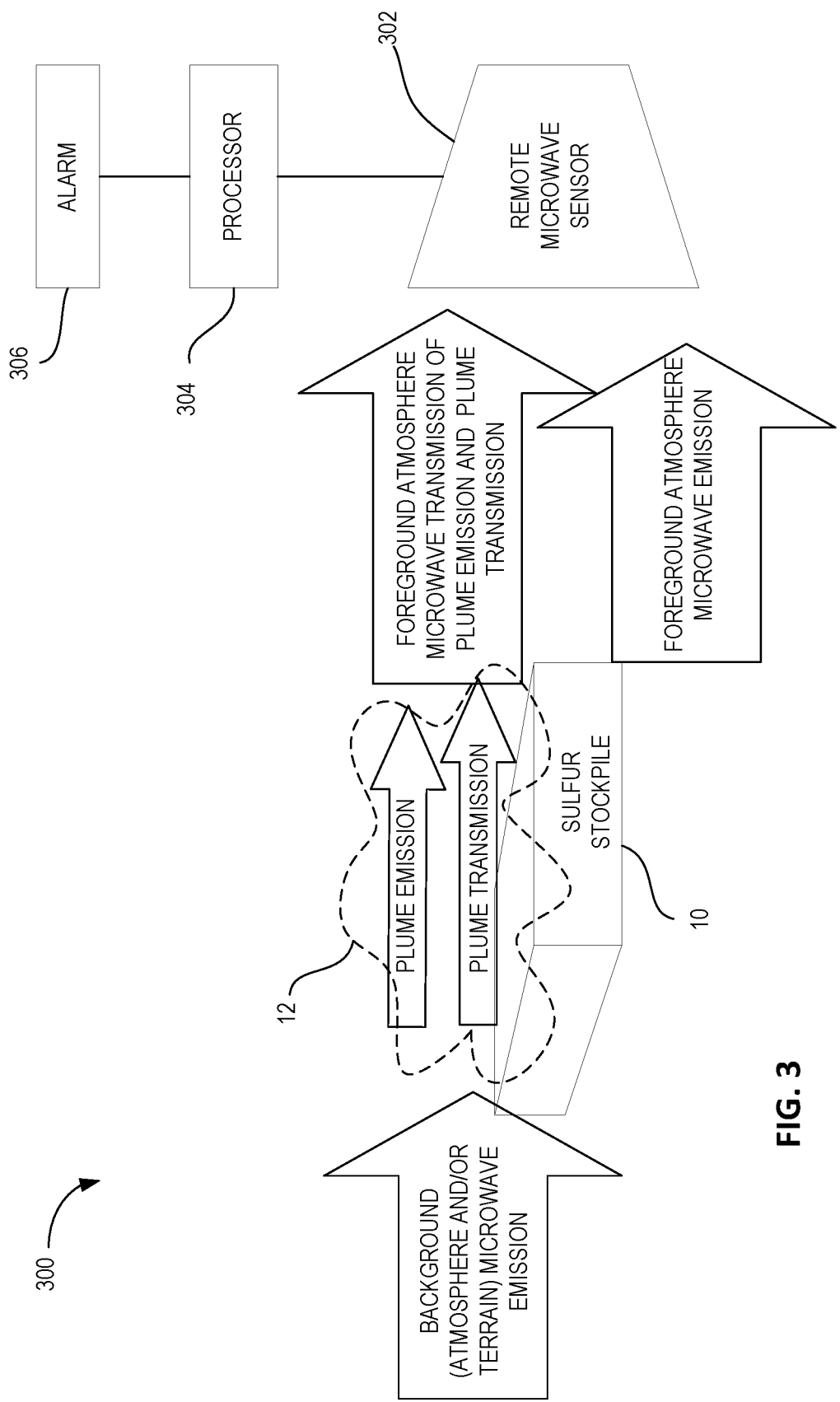
FIG. 3 is a schematic view of an alternate system for detecting sulfur fires as disclosed herein.

FIG. 3 illustrates an alternate embodiment of the sulfur fire-watch and detection system 300. For the embodiment of FIG. 3, the features are referred to using similar reference numerals under the "3xx" series of reference numerals, rather than "1xx" as used in the embodiment of FIG. 1. Accordingly, certain features of system 300 that were already described above with respect to system 100 of FIG. 1 may be described in lesser detail, or may not be described at all. The sensor 302 may be a passive microwave sensor that receives radiation emitted from the background atmosphere or terrain, located behind the sulfur dioxide plume 12, radiation emitted from the sulfur stockpile 10 within the storage area, and radiation emitted from the foreground atmosphere and terrain, which is located between the sensor 102 and the sulfur stockpile 10. Detecting sulfur dioxide gas with a passive microwave sensor may be similar to sulfur dioxide gas detection with an infrared sensor described above using sensor 102, where the sulfur dioxide gas may absorb radiation at various frequencies where the microwave sensor 302 may detect the resulting transmission or emission based upon the absorption properties of the sulfur dioxide gas. The primary difference being that sensor 302 is set up to receive radiation within the microwave spectrum, in particular within a wavelength from approximately 100 cm (39.4 in.) and 0.1 cm (0.039 in.) or, in other words, within a frequency range of 0.3 GHz and 300 GHz. In the microwave spectrum, the longer wavelengths may penetrate the plume 12 or other obstacles better. The refractivity of the sulfur dioxide within the microwave spectrum may be used to detect and/or determine how much sulfur dioxide is present as the absorptivity of sulfur dioxide and other gases changes with frequency. One skilled in the art will recognize that the atmospheric composition of some planetary atmospheres is determined by use of passive microwave remote sensing. As such, a microwave sensor 302 may be adapted to sulfur dioxide gas detection and/or determination for a sulfur fire-watch system.

The sensor 302 may measure the atmosphere's emissivity and the processor 304 may track any changes in the emissivity over a predetermined time period to determine if a sulfur dioxide plume is present in the atmosphere. As known to one skilled in the art, changes in the atmospheric emissivity may indicate the presence of sulfur dioxide in certain wavelengths, and emissivity is a function of the dielectric constant of the material. The dielectric constant of different materials is also known as relative permittivity of the material. A microwave sensor may operate in the range 0.3 GHz and 35 GHz (100 cm (39.4 in.) and 0.86 cm (0.34 in.)). Atmospheric attenuation of microwave radiation may primarily through absorption by water vapor and oxygen, where absorption is strongest at the shortest wavelength. Attenuation may be very low for a wavelength greater than 3 cm (1.18 in.) (i.e. a frequency less than 10 GHz). In general, microwave radiation is not greatly influenced by cloud or fog, especially for wavelength greater than 3 cm (1.18 in.). The atmosphere's dielectric constant, relative permittivity or emissivity may change depending upon the concentration of gases contained, such as sulfur dioxide. For example, dielectric constant, relative permittivity, of air is 1, compared to sulfur dioxide's dielectric constant, or relative permittivity, which may range approximately from 15.0 (at 0° C. (32° F.)) to 17.6 (at −20° C. (−4° F.)), so as sulfur dioxide concentration increases the atmosphere's dielectric constant relative permittivity may locally increase up to approximately fifteen-times greater.

Additionally, elemental sulfur's dielectric constant and emissivity may change with temperature. For example, sulfur appears to be bright-yellow at room temperature, and changes to a golden color above about 120° C. (248° F.), and changes to a dark red color above around 200° C. (392° F.). As some sulfur stockpiles 10 may be decades old or generally stationary, the sulfur stockpile 10 may have emissivity differences based on the environmental conditions around the stockpile 10. Stockpiled sulfur's dielectric constant may range approximately from 1.6 to 1.7, or may be less than sulfur powder's dielectric constant that is approximately 3.6. Liquid sulfur's dielectric constant may be approximately 3.5 (at 118° C. (244° F.)). Dielectric constants for ice are lower, and for water are greater. For example, water is approximately 88.0 (at 0° C. (32° F.)). Change of stockpiled sulfur's surface emissivity value, or change of dielectric constant value from approximately 1.6 to 3.5, may indicate production of liquid sulfur, which can forewarn of a sulfur fire as a sulfur fire requires liquid sulfur, or enough vaporized sulfur to fuel combustion.

For fire-watch purposes, the sensor 302 may take readings at predetermined time intervals such that the processor 304 may detect a change in the atmospheric conditions. The processor 304 may not necessarily differentiate between the various gases, or trace gases, in a plume, as long as the processor 304 can determine that sulfur dioxide is present upon and in some embodiments greater than a predetermined limit. Upon determining the sulfur dioxide is present and/or above the predetermined limit, the processor 304 may send a signal to the alarm. For example, the predetermined limit for sulfur dioxide gas may be if the sulfur dioxide has a concentration that forms greater than approximately 10 ppm, or greater than 50 ppm, or greater than 100 ppm. Using a microwave sensor may allow for the sulfur dioxide gas to be measured from greater distances such that the sulfur dioxide may be sensed from a ground-based, airborne, or space-borne microwave sensor. A ground-based microwave sensor, relatively may measure sulfur dioxide within the sulfur plume 12 (within a range of greater than approximately 1000 meters (0.62 miles), or greater than 5000 meters (3.1 miles), or in some cases, greater than 20,000 meters (12.4 miles)), which may be useful for stockpile fire-watch for detection of relatively large plumes or relatively large exposed sulfur surface.

Figure 4:
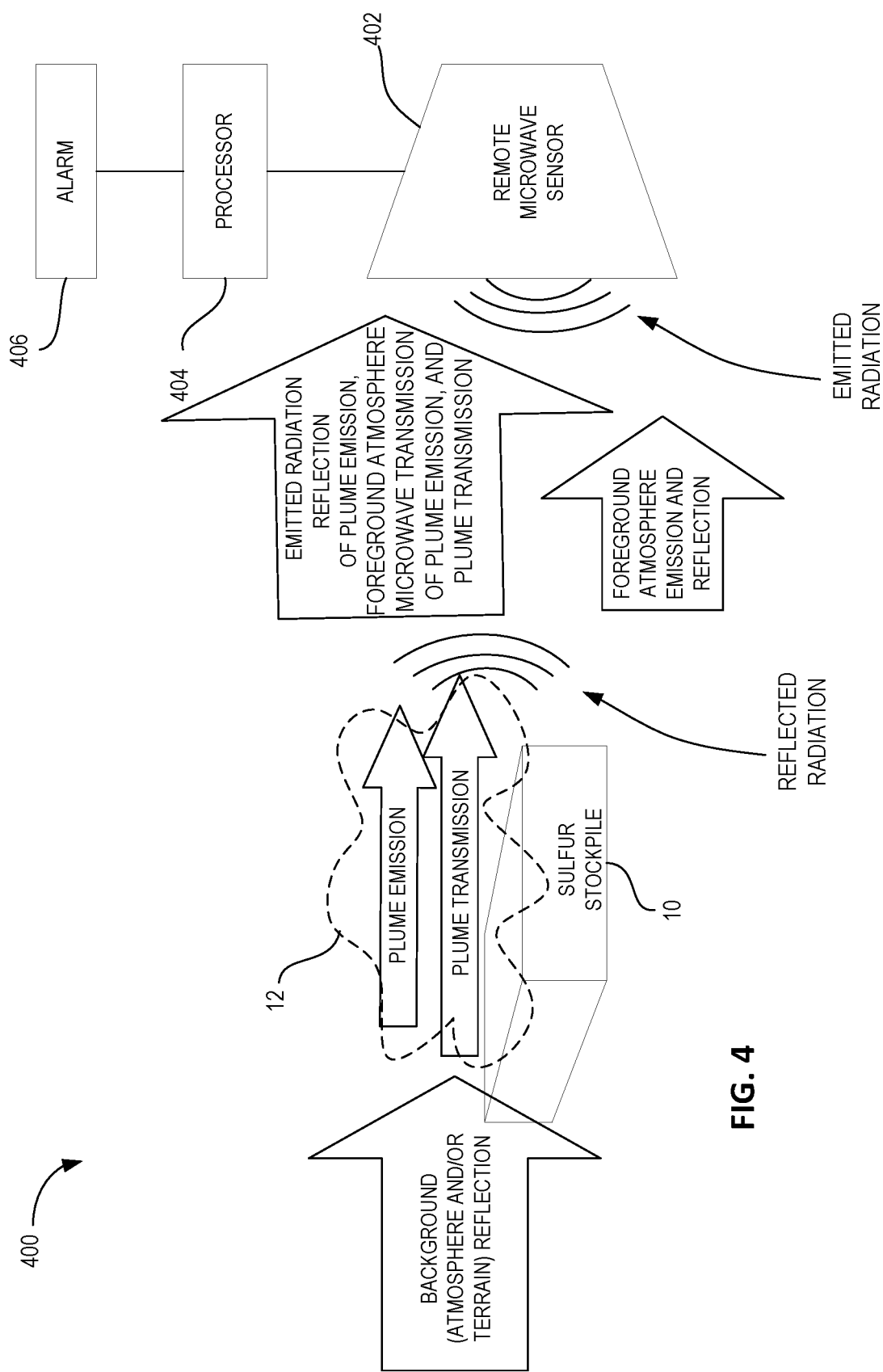
FIG. 4 is a schematic view of an alternate system for detecting sulfur fires as disclosed herein.

FIG. 4 illustrates another alternate embodiment of the fire-watch and detection system 400. For the embodiment of FIG. 4, the features are referred to using similar reference numerals under the "4xx" series of reference numerals, rather than "1xx" as used in the embodiment of FIG. 1. Accordingly, certain features of the system 400 that were already described above with respect to system 100 of FIG. 1 and system 300 of FIG. 3 may be described in lesser detail, or may not be described at all. The sensor 402 may be an active microwave sensor that includes an antenna that emits radiation (that may be constant frequency or may be pulses or may be modulating frequency) toward the sulfur stockpile 10 and sulfur dioxide plume 12 (if present) and then receives and measures the radiation that is reflected or backscattered from the emitted radiation. The system 400 may operate similar to the system 300 as described above. Similar to system 300, the sensor 402 may be optimized to receive radiation within the microwave spectrum, in particular with a frequency of within a range of 0.3 GHz and 300 GHz, the sensor 402 may take readings at predetermined time intervals such that the processor 404 may detect a change in the atmospheric conditions. The processor 404 may not necessarily differentiate between the various gases, or trace gases, in a plume, as long as the processor 404 can determine that sulfur dioxide is greater than a predetermined limit.

Upon determining the sulfur dioxide is present and/or above the predetermined limit, the processor 404 may send a signal to the alarm. For example, the predetermined limit for sulfur dioxide gas may be if the sulfur dioxide has a concentration that forms greater than approximately 10 ppm, or greater than 50 ppm, or greater than 100 ppm.

As discussed above, the sensor 402 may be an active microwave sensor such that the microwave sensing method and device may detect changes in radar reflection, refraction, and scattering properties of the sulfur dioxide plume 12, with respect to the surrounding atmosphere. For example, one possible sensor may be an X-band marine radar with a peak power output of approximately 6 kW, a minimum detectable range of approximately 27 m (88.6 feet), and a range of approximately 0.2 kilometers (0.124 miles) to 3 kilometers (1.86 miles) at a pulse length of approximately 0.08 microseconds and pulse repetion rate of approximately 2100 Hertz. Alternatively, the range may be approximately 3 kilometers (1.86 miles) to 6 kilometers (3.73 miles) at a pulse length of approximately 0.3 microseconds and pulse repetion rate of approximately 1200 Hertz. Alternatively, the range may be approximately 6 kilometers (3.73 miles) to 119 kilometers (73.9 miles) at a pulse length of approximately 0.8 microseconds and pulse repetion rate of approximately 600 Hertz.

While various embodiments have been described, it will be apparent to those of ordinary skill in the art that many more embodiments and implementations are possible that are within the scope of the claims. The various dimensions described above are merely exemplary and may be changed as necessary. Accordingly, it will be apparent to those of ordinary skill in the art that many more embodiments and implementations are possible that are within the scope of the claims. Therefore, the embodiments described are only provided to aid in understanding the claims and do not limit the scope of the claims.

We claim:

1. A system for detecting sulfur fires comprising:
   a sensor located a predetermined distance from a sulfur stockpile, wherein the sensor has a field of view of the sulfur stockpile and is configured to receive radiation emitted from the sulfur stockpile;
   one or more processors configured to receive data from the sensor; and
   a non-transitory, computer-readable medium storing computer-executable instructions that, when executed by the one or more processors, causes the one or more processors to:
   receive data from the sensor;
   determine if sulfur dioxide is present in the field of view using thermal contrast imaging;
   calculate a slant column density of a sulfur plume in the field of view;
   compare the calculated slant column density to a predetermined limit of sulfur dioxide gas; and
   send a signal to an alarm upon determining that the calculated slant column density is greater than the predetermined limit of sulfur dioxide gas.

2. The system for detecting sulfur fires according to claim 1, wherein the predetermined limit of sulfur dioxide gas is at a path concentration above 1,000 ppm-m.

3. The system for detecting sulfur fires according to claim 1, wherein the non-transitory, computer readable medium stores computer readable instructions that, when executed by the one or more processors, further cause the one or more processors to:
   determine a stockpile temperature of a portion of the sulfur stockpile within the field of view; and
   compare the stockpile temperature to a predetermined threshold temperature,
   wherein upon determining that the stockpile temperature is greater than the predetermined threshold temperature and upon determining that the calculated slant column density is greater than the predetermined limit of sulfur dioxide gas, the one or more processors are caused to send the signal to the alarm.

4. The system for detecting sulfur fires according to claim 3, wherein the predetermined threshold temperature is 1900 degrees Celsius.

5. The system for detecting sulfur fires according to claim 1, wherein the sensor is connected to a mount that is configured to move the sensor such that the field of view of the sensor moves in a predetermined scan schedule.

6. The system for detecting sulfur fires according to claim 1, wherein the sensor is an infrared sensor.

7. The system for detecting sulfur fires according to claim 1, wherein the sensor is capable of receiving electromagnetic radiation within a wavelength range of 1 m and 16 m.

8. The system for detecting sulfur fires according to claim 1, wherein the predetermined distance from the sulfur stockpile is within 17 kilometers.

9. The system for detecting sulfur fires according to claim 1, wherein a plurality of sensors including the sensor are evenly spaced apart around the sulfur stockpile.

10. The system for detecting sulfur fires according to claim 9, wherein the plurality of sensors comprise three sensors.

11. The system for detecting sulfur fires according to claim 5, wherein the predetermined scan schedule is a range height indicator scan using a fixed azimuth angle while varying an elevation angle.

12. The system for detecting sulfur fires according to claim 5, wherein the predetermined scan schedule is a plan position indicator scan using a fixed elevation angle while varying an azimuth angle.

13. The system for detecting sulfur fires according to claim 5, wherein moving the field of view of the sensor in the predetermined scan schedule comprises varying an azimuth angle and/or an elevation angle.

14. The system for detecting sulfur fires according to claim 1, wherein the system transmits the signal wirelessly to a remote computer.

15. The system for detecting sulfur fires according to claim 1, wherein the sensor is a microwave sensor.

16. The system for detecting sulfur fires according to claim 13, wherein the sensor is an active microwave sensor, wherein the active microwave sensor detects radiation that is emitted by the sulfur stockpile and other objects within the field of view.

17. The system for detecting sulfur fires according to claim 13, wherein the sensor is a passive microwave sensor, wherein the passive microwave sensor detects radiation that is emitted or reflected by the sulfur stockpile and other objects within the field of view.

* * * * *